US011389049B2

(12) United States Patent
Araki

(10) Patent No.: US 11,389,049 B2
(45) Date of Patent: Jul. 19, 2022

(54) ENDOSCOPE AND MANUFACTURING METHOD OF ENDOSCOPE

(71) Applicant: OLYMPUS CORPORATION, Hachioji (JP)

(72) Inventor: Kohei Araki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 385 days.

(21) Appl. No.: 16/152,032

(22) Filed: Oct. 4, 2018

(65) Prior Publication Data

US 2019/0029494 A1    Jan. 31, 2019

Related U.S. Application Data

(63) Continuation of application No. PCT/JP2017/021181, filed on Jun. 7, 2017.

(30) Foreign Application Priority Data

Jun. 27, 2016    (JP) .............................. JP2016-126320

(51) Int. Cl.
*A61B 1/00* (2006.01)
*A61B 1/06* (2006.01)
*G02B 23/24* (2006.01)

(52) U.S. Cl.
CPC .......... *A61B 1/0008* (2013.01); *A61B 1/0011* (2013.01); *A61B 1/00137* (2013.01);
(Continued)

(58) Field of Classification Search
CPC . A61B 1/0008; A61B 1/0011; A61B 1/00137; A61B 1/0676; A61B 1/0684;
(Continued)

(56) References Cited

U.S. PATENT DOCUMENTS 4,945,894 A * 8/1990 Kawashima ....... A61B 1/00165
600/129
2002/0010385 A1 * 1/2002 Ishibiki .............. A61B 1/00105
600/139
(Continued)

FOREIGN PATENT DOCUMENTS

CN          103354727 A       10/2013
JP          2010069096 A  *   4/2010
(Continued)

OTHER PUBLICATIONS

Jan. 1, 2019 International Preliminary Report on Patentability issued in International Patent Application PCT/JP2017/021181.
(Continued)

*Primary Examiner* — Michael J Carey
*Assistant Examiner* — Stephen Floyd London
(74) *Attorney, Agent, or Firm* — Oliff PLC

(57) ABSTRACT

An endoscope has a distal end constituting portion provided at a distal end of an insertion section to be inserted into a subject, a distal end cover that is integrally formed to include a translucent plate-shaped first member and a second member arranged around the first member and that is attached to an end surface of the distal end constituting portion, and a resin portion that is annularly applied to a portion including a boundary portion between the first member and the second member and that prevents transmission of a fluid.

18 Claims, 5 Drawing Sheets

(52) U.S. Cl.
CPC .......... *A61B 1/0676* (2013.01); *A61B 1/0684* (2013.01); *G02B 23/2423* (2013.01); *G02B 23/2469* (2013.01)

(58) Field of Classification Search
CPC ... A61B 1/00096; A61B 1/06; A61B 1/00165; A61B 1/00064; A61B 1/00071; A61B 2017/00296; A61B 1/00121; A61B 1/00131; G02B 23/2469; G02B 23/2423; G02B 23/2476; G02B 7/025; Y10S 600/92
See application file for complete search history.

(56) References Cited

U.S. PATENT DOCUMENTS

| | | | |
|---|---|---|---|
| 2006/0183977 A1* | 8/2006 | Ishigami | A61B 1/0684 600/179 |
| 2007/0118020 A1* | 5/2007 | Miyagi | A61B 1/0623 600/177 |
| 2008/0300457 A1* | 12/2008 | Hosaka | A61B 1/12 600/110 |
| 2009/0129051 A1* | 5/2009 | Bausewein | A61B 1/0676 362/84 |
| 2010/0022841 A1* | 1/2010 | Takahashi | G02B 7/025 600/162 |
| 2010/0152540 A1* | 6/2010 | Tanoue | G02B 23/2469 600/175 |
| 2012/0209072 A1* | 8/2012 | Oue | G02B 23/2476 600/129 |
| 2013/0274554 A1* | 10/2013 | Sato | A61B 1/00096 600/121 |
| 2013/0301148 A1* | 11/2013 | Breidenthal | G02B 7/02 359/819 |
| 2014/0078287 A1* | 3/2014 | Ichihashi | A61B 1/00027 348/82 |
| 2015/0062316 A1* | 3/2015 | Haraguchi | A61B 1/00009 348/65 |
| 2015/0150441 A1* | 6/2015 | Ouyang | A61B 10/04 600/109 |
| 2015/0240137 A1* | 8/2015 | Yokoyama | G02B 23/2476 600/133 |
| 2015/0316742 A1* | 11/2015 | Jono | A61B 1/055 348/76 |

FOREIGN PATENT DOCUMENTS

| | | |
|---|---|---|
| JP | 5298260 B1 | 9/2013 |
| JP | 2014-2300 A | 1/2014 |
| JP | 2014002300 A * | 1/2014 |
| JP | 2015-42219 A | 3/2015 |
| WO | 2013/054753 A1 | 4/2013 |
| WO | WO-2013128681 A1 * | 9/2013 ........... A61B 1/0011 |

OTHER PUBLICATIONS

Jan. 30, 2018 Office Action issued in Japanese Patent Application No. 2017-563138.
May 7, 2020 Office Action issued in Chinese Patent Application No. 201780023311.1.
Sep. 5, 2017 Interntional Search Report issued in International Patent Application PCT/JP2017/021181.
Feb. 10, 2021 Office Action issued in Chinese Patent Application No. 201780023311.1.

* cited by examiner

ENDOSCOPE AND MANUFACTURING METHOD OF ENDOSCOPE

CROSS-REFERENCE TO RELATED APPLICATIONS

This application is a Continuation Application of PCT Application No. PCT/JP2017/021181, filed Jun. 7, 2017 and based upon and claiming the benefit of priority from prior Japanese Patent Application No. 2016-126320, filed Jun. 27, 2016, the entire contents of all of which are incorporated herein by reference.

BACKGROUND OF THE INVENTION

1. Field of the Invention

The present invention relates to an endoscope having a distal end cover.

2. Description of the Related Art

For example, Patent Literature 1 discloses an endoscope in which a distal end cover is provided at a distal end of the endoscope. The distal end cover is adhered to a distal end rigid portion at the distal end of the endoscope. This distal end cover is made by integrating a first molded portion formed of a transparent first resin member having an illumination window portion and a second molded portion formed of a second resin member having an external shape, by, for example, two-color molding.

CITATION LIST

Patent Literature

Patent Literature 1: Japanese Patent No. 5298260

BRIEF SUMMARY OF THE INVENTION

The endoscope according to one aspect of the present invention includes a distal end constituting portion provided at a distal end of an insertion section to be inserted into a subject, a distal end cover that is integrally formed to include a translucent plate-shaped first member and a second member arranged around the first member and that is attached to an end surface of the distal end constituting portion, and a resin portion that is annularly applied to a portion including a boundary portion between the first member and the second member and that prevents transmission of a fluid.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

First Embodiment

Figure 1:
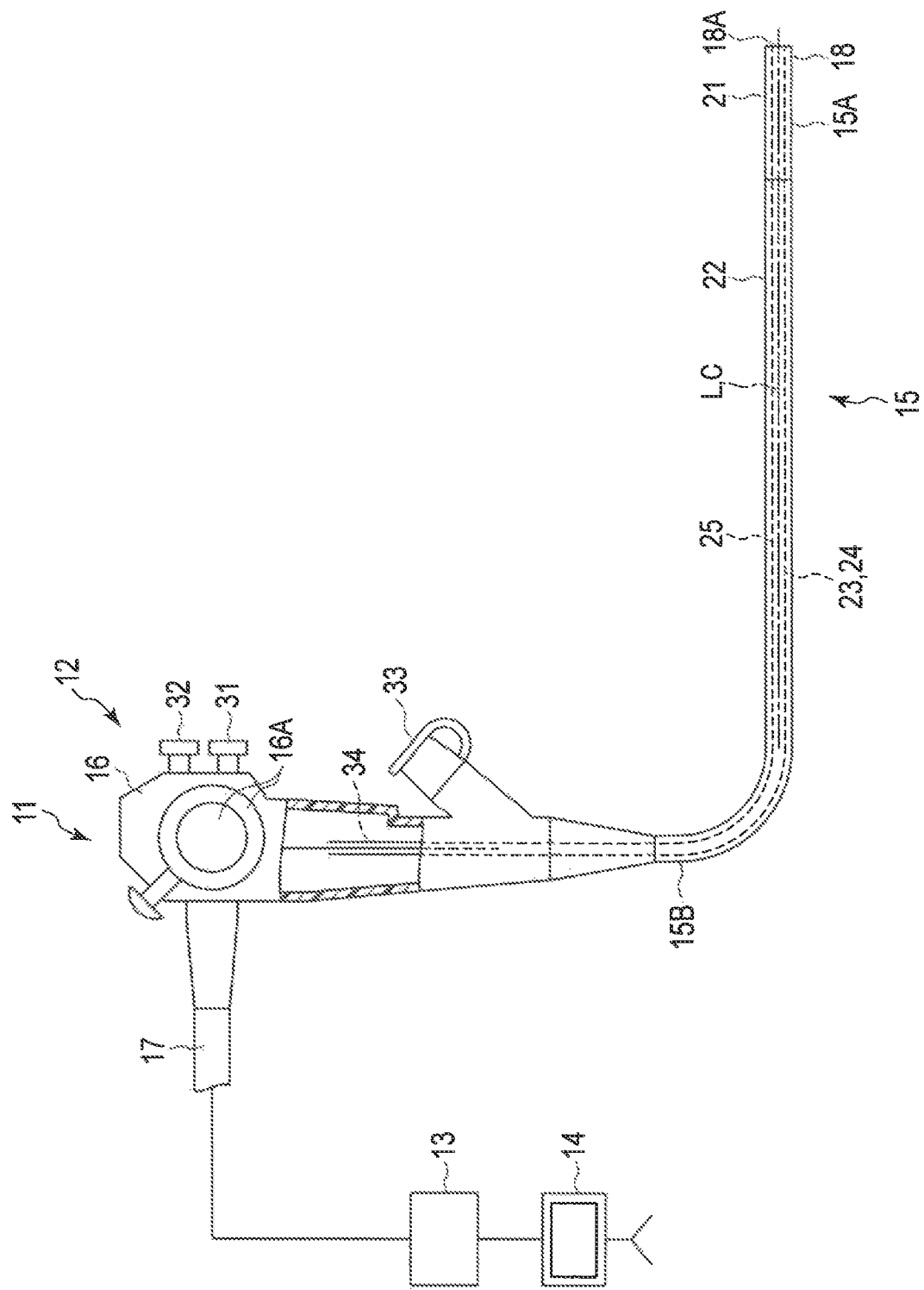
FIG. 1 is a schematic diagram showing an endoscope system and an endoscope according to a first embodiment.

An endoscope system according to a first embodiment will be described with reference to FIGS. 1 to 4. As shown in FIG. 1, an endoscope system 11 includes an endoscope 12, an endoscope controller 13 (a control unit) that performs image processing based on a subject image taken by the endoscope 12, and a display unit 14 (a monitor) that displays an image generated by the image processing at the endoscope controller 13.

Figure 2:
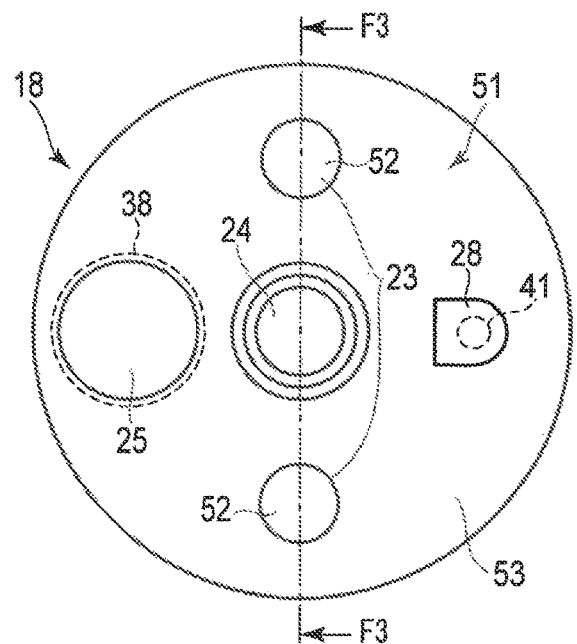
FIG. 2 is a schematic diagram showing an insertion section of the endoscope shown in FIG. 1 from an end surface side.

As shown in FIGS. 1 and 2, the endoscope 12 (an insertion instrument) has an insertion section 15 inserted into a tube line such as a lumen of a subject along a longitudinal direction L (a central axis C), an operating unit 16 provided at a proximal end 15B of the insertion section 15 and gripped by a user, and a universal cord 17 extended from the operating unit 16.

As shown in FIG. 1, the insertion section 15 has a distal end constituting portion 18, a bending portion 21, and a tube section 22 in order, from a distal end 15A of the insertion section 15 toward the proximal end 15B of the insertion section 15. The tube section 22 may be a tube section with flexibility, which is a so-called flexible scope. With a known mechanism, the bending portion 21 can be bent in multiple directions such as two directions or four directions by a knob 16A of the operating unit 16.

As shown in FIGS. 1 and 2, the endoscope 12 has an illumination optical system 23 for illuminating inside the subject, an objective optical system 24 in an imaging unit, and a treatment tool insertion channel 25 from which a treatment tool such as a forceps is drawn out. Although not shown, the endoscope 12 also has an air/water supply mechanism that supplies a fluid to a subject area in the subject, and a suction mechanism. The air/water supply mechanism has an air/water supply channel 28 at the distal end of the insertion section 15. The air/water supply mechanism is operated by a first button 31 of the operating unit 16. The suction mechanism communicates with the treatment tool insertion channel 25, and is operated by a second button 32 of the operating unit 16.

The illumination optical system 23 and the objective optical system 24 are inserted through the distal end constituting portion 18 of the insertion section 15 of the endoscope 12, the bending portion 21, and the tube section 22, the operating unit 16, and the universal cord 17.

The distal end of the treatment tool insertion channel 25 is opened at the distal end constituting portion 18 of the insertion section 15 of the endoscope 12, and the proximal end of the treatment tool insertion channel 25 is opened near a proximal end portion of the tube section 22 of the insertion section 15 or in the operating unit 16. Herein, as shown in FIG. 1, an opening (not shown) of the proximal end of the treatment tool insertion channel 25 is in the operating unit 16, and a forceps plug 33 is attachable to and detachable from this opening through a metal cap. The distal end of a tube of the treatment tool insertion channel 25 is fixed to the distal end constituting portion 18 through a metal cap. The tube of the treatment tool insertion channel 25 branches into, for example, a known suction path 34 inside the operating unit 16, as shown in FIG. 1. The suction path 34 is connected to the second button 32. By pressing the second button 32, the aspirate is discharged from the hole portion at the distal end of the treatment tool insertion channel 25 via the tube, the suction path 34, and the universal cord 17.

Figure 3:
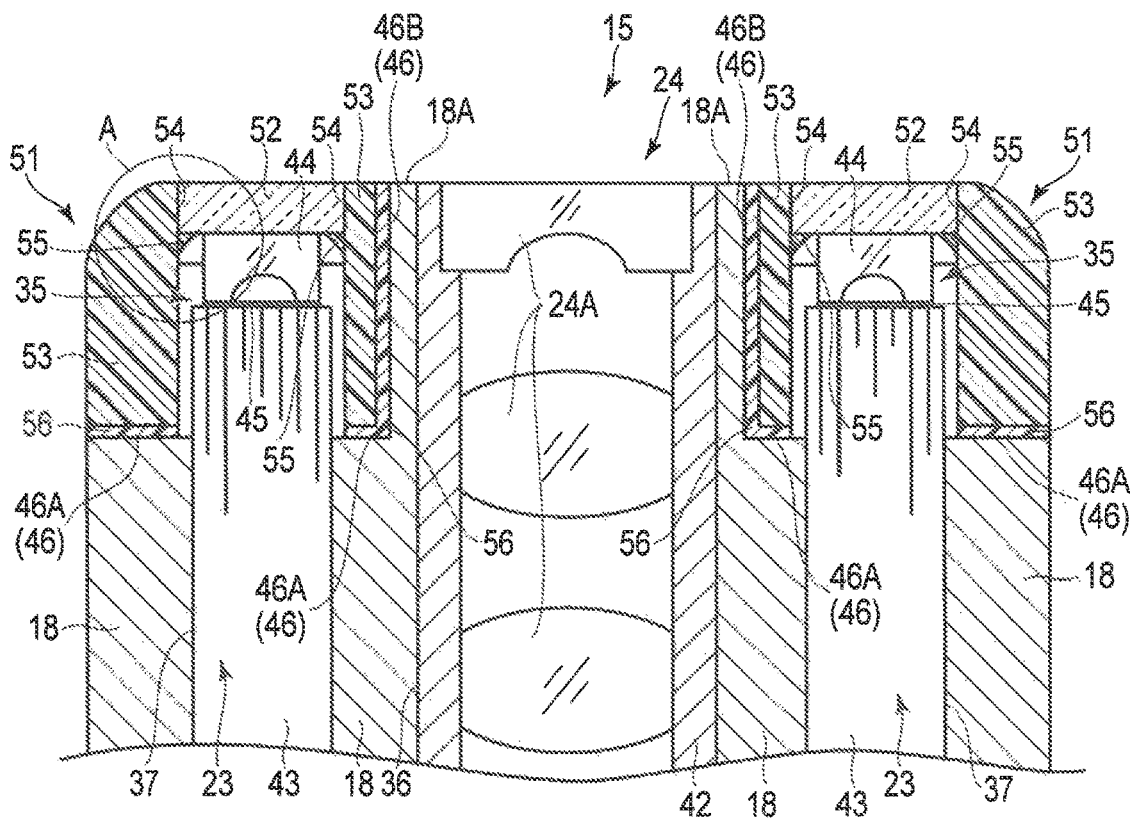
FIG. 3 is a cross-sectional view taken along line F3-F3 shown in FIG. 2.

The distal end constituting portion 18 is, for example, a cylindrical body made of metal such as stainless steel. The distal end constituting portion 18 is arranged at the distal end of the insertion section 15 to be inserted into the subject. As shown in FIGS. 2 and 3, the distal end constituting portion 18 is provided with, for example, a recessed portion 35, a lens frame hole 36, a pair of light guide holes 37, a treatment channel hole 38, and an air/water supply hole 41. The distal end constituting portion 18 has a lens frame hole 42 on the periphery of the lens frame hole 36. Inside the lens frame 42, optical members such as a plurality of lenses 24A constituting the objective optical system 24 are disposed.

As shown in FIG. 3, the illumination optical system 23 has a light guide fiber bundle 43 inserted through the light guide hole 37, and an illumination lens 44. The light guide fiber bundle 43 can guide the light from a light source provided on the side of the endoscope controller 13 to the illumination lens 44 located at a distal end of the light guide fiber bundle 43. The illumination lens 44 is adhered and fixed to a distal end surface of the light guide fiber bundle 43 by an optical adhesive 45. The illumination lens 44 is an example of an illumination unit that emits illumination light.

The recessed portion 35 is recessed from a distal end surface 18A of the distal end constituting portion 18 (the insertion section 15). The recessed portion 35 has a defining surface 46 (a bottom surface 46A and a side surface 46B) that defines its recessed area. A distal end portion of the light guide fiber bundle 43 and the illumination lens 44 (an illumination unit) are arranged in the recessed portion 35.

The distal end cover 51 is attached to the distal end constituting portion 18 in a manner so that the distal end cover 51 is flush with the distal end surface 18A (an end surface) of the distal end constituting portion 18. As shown in FIGS. 2 and 3, the distal end cover 51 is entirely in a ring shape (an annular shape), and covers the majority of the distal end constituting portion 18 except for the illumination optical system 23 located at the center portion. As shown in FIG. 3, the distal end cover 51 has a translucent plate-like (discoid) first member 52, a second member 53 arranged to surround the periphery of the first member 52, a boundary portion 54 located therebetween, and a resin portion 55 provided in a manner so that the resin portion 55 corresponds to the boundary portion 54. The second member 53 of the distal end cover 51 and the distal end constituting portion 18 are adhered by an adhesive 56. The adhesive 56 is preferably composed of the same material (a thermosetting epoxy adhesive) as the resin portion 55 which will be described later. The adhesive 56 is an example of the resin portion in the present invention.

The first member 52 and the second member 53 of the distal end cover 51 are integrally formed by, for example, injection molding (so-called two-color molding) of resin. The first member 52 faces the illumination lens 44. The first member 52 is formed of, for example, polysulfone, and the second member 53 is arranged in immediate contact with and so as to surround the periphery of the first member 52. The second member 53 is formed of, for example, polysulfone containing, for example, a black pigment/coloring or carbon. The first member 52 and the second member 53 may be formed of different materials from each other. The first member 52 is constituted by, for example, a translucent plate (a transparent flat plate), and may be, for example, a flat plate of which at least one surface has a recessed shape. The second member 53 is not translucent, and prevents transmission of light.

The resin portion 55 is provided on a side (the inner side) facing the distal end constituting portion 18. The resin portion 55 is annularly applied to a portion including the boundary portion 54, in a manner so that the resin portion 55 corresponds to the boundary portion 54. Herein, "annular" preferably means that the ring continues without interruption, but this "annular" state is not limited to this meaning. For example, "annular" may be "substantially annular" in which the ring is interrupted at one or more positions. The resin portion 55 is an example of the resin portion in the present invention.

Figure 4:
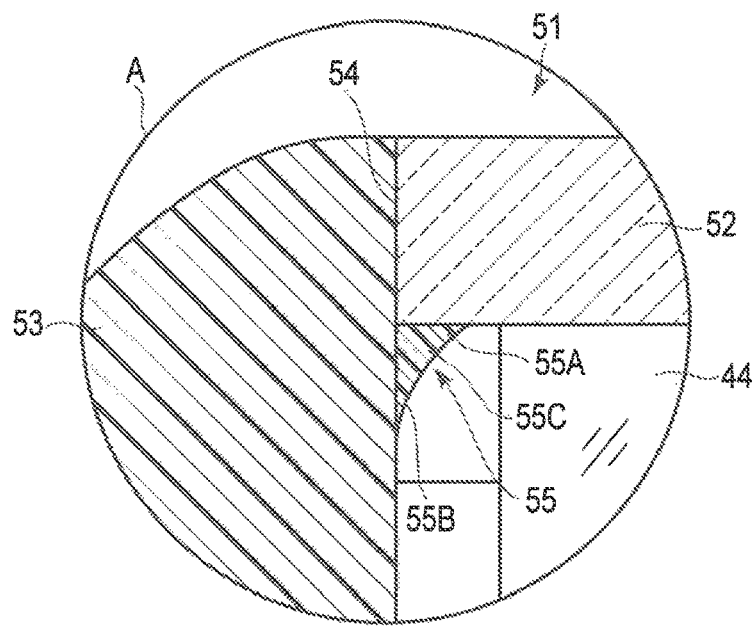
FIG. 4 is an enlarged cross-sectional view of a portion A shown in FIG. 3.

As shown in FIG. 4, the resin portion 55 is adhered to the first member 52 and the second member 53 in a manner so that the resin portion 55 extends over the first member 52 by a first fillet portion 55A and extends over the second member 53 by a second fillet portion 55B that is on the opposite side from the first fillet portion. The adhesive pool 55C of the resin portion 55 located between the first fillet portion 55A and the second fillet portion 55B is arranged at a position substantially overlapping with the boundary portion 54. For the resin portion 55, for example, a thermosetting epoxy adhesive is preferably used in order to securely form the adhesive pool 55C at a position corresponding to the boundary portion 54, and to maintain the joining strength after hardening. The resin portion 55 formed of, for example, a thermosetting epoxy adhesive can prevent transmission of fluid (e.g., moisture).

On the distal end cover 51, the resin portion 55 is applied and is subjected to thermal hardening processing in advance. Then, as shown in FIG. 3, the distal end cover 51 is adhered to the recessed portion 35 with the adhesive 56. For the adhesive 56, a thermosetting epoxy adhesive is preferably used, similarly to the resin portion 55.

A method of adhering the distal end cover 51 of the endoscope 12 of the first embodiment (a method of manufacturing an endoscope) will be described.

After completing the injection molding (two-color molding) of the distal end cover 51, an operator (or a robot) annularly applies a thermosetting epoxy adhesive as a material of the resin portion 55 on the boundary portion 54 on the side facing the distal end constituting portion 18, as shown in FIGS. 3 and 4. After the adhesive is thermally hardened to form the resin portion 55, the operator applies the adhesive 56 (a thermosetting epoxy adhesive) to the defining surface 46 of the recessed portion 35, or to a portion of the distal end cover 51 which abuts the defining surface 46, and covers the recessed portion 35 with the distal end cover 51. In this state, the adhesive 56 is thermally hardened to adhere the distal end cover 51 to the distal end constituting portion 18. With the above, the operation of adhering the distal end cover 51 to the distal end constituting portion 18 is completed.

According to the first embodiment, the following can be said. An endoscope includes: a distal end constituting portion 18 provided at a distal end of an insertion section 15 to be inserted into a subject; a distal end cover 51 that is integrally molded to include a translucent plate-like first member 52 and a second member 53 arranged around the first member 52, and that is attached to the distal end constituting portion 18; and a resin portion 55 that is annularly applied to a portion including a boundary portion 54 between the first member 52 and the second member 53, and that prevents transmission of a fluid.

Generally, in a structure in which the first member 52 and the second member 53 are merely joined, if a stress is applied to the boundary portion 54 due to an external shock or sterilization, the boundary portion 54 may be minutely deformed, which leads to cracks in the boundary portion 54. Once cracks are produced, the joining length of the joining of the first member 52 and the second member 53 is shortened and the joining strength is reduced; accordingly, cracks may grow and the entire boundary portion 54 may be cracked.

According to the above configuration, the first member 52 and the second member 53 are joined by the resin portion 55, and even if a stress is applied to the boundary portion 54 due to an external shock or sterilization, the boundary portion 54 between the first member 52 and the second member 53 is not easily deformed because of the function of the resin portion 55. Therefore, even if the stress is applied, it is possible to reduce the risk of producing cracks in the boundary portion 54 between the first member 52 and the second member 53. Furthermore, even if an unexpected stress applied to the distal end cover 51 due to, for example, a user's handling error produces cracks in the boundary portion 54 between the first member 52 and the second member 53, the resin portion 55 serves as a protection barrier and can avoid entrance of a fluid such as moisture from the outside of the endoscope 12.

The resin portion 55 is applied to the distal end cover 51 on a side facing the distal end constituting portion 18. According to this configuration, the resin portion 55 is not exposed to, for example, a chemical solution when sterilizing the endoscope 12, and deterioration of the resin portion 55 can be prevented as much as possible. Therefore, high joining strength of the boundary portion 54 can be stably maintained for a long period of time.

The second member 53 is arranged in immediate contact with and so as to surround the periphery of the first member 52, and prevents transmission of light. According to this configuration, it is possible to integrally form a portion that transmits light and a portion that does not transmit light.

An illumination unit that emits illumination light is arranged on the distal end constituting portion 18, and the first member 52 faces the illumination unit. According to this configuration, it is possible to securely fix the first member 52 that serves as a lens portion for illumination by the resin portion 55, and to reduce the risk of forming cracks near the first member 52.

The recessed portion 35 defined by the defining surface 46 is provided in a portion where the illumination unit is arranged in the distal end constituting portion 18. The resin portion is applied between the defining surface 46 of the recessed portion 35 and the distal end cover 51 to adhere the defining surface 46 to the distal end cover 51. According to this configuration, the aforementioned resin portion 55 and the adhesive 56 that adheres the defining surface 46 to the distal end cover 51 can be formed with a common material, and it is not necessary to form the resin portion 55 with a special material. As a result, it is possible to reduce the manufacturing cost for forming the resin portion 55, and to reduce the manufacturing cost of the entire endoscope 12.

The first member 52 and the second member 53 are two-color molded resin. According to this configuration, a structure in which the first member 52 and the second member 53 are integrated can be easily formed. As a result, the number of parts and the number of assembling steps can be reduced.

First Modification

Figure 5:
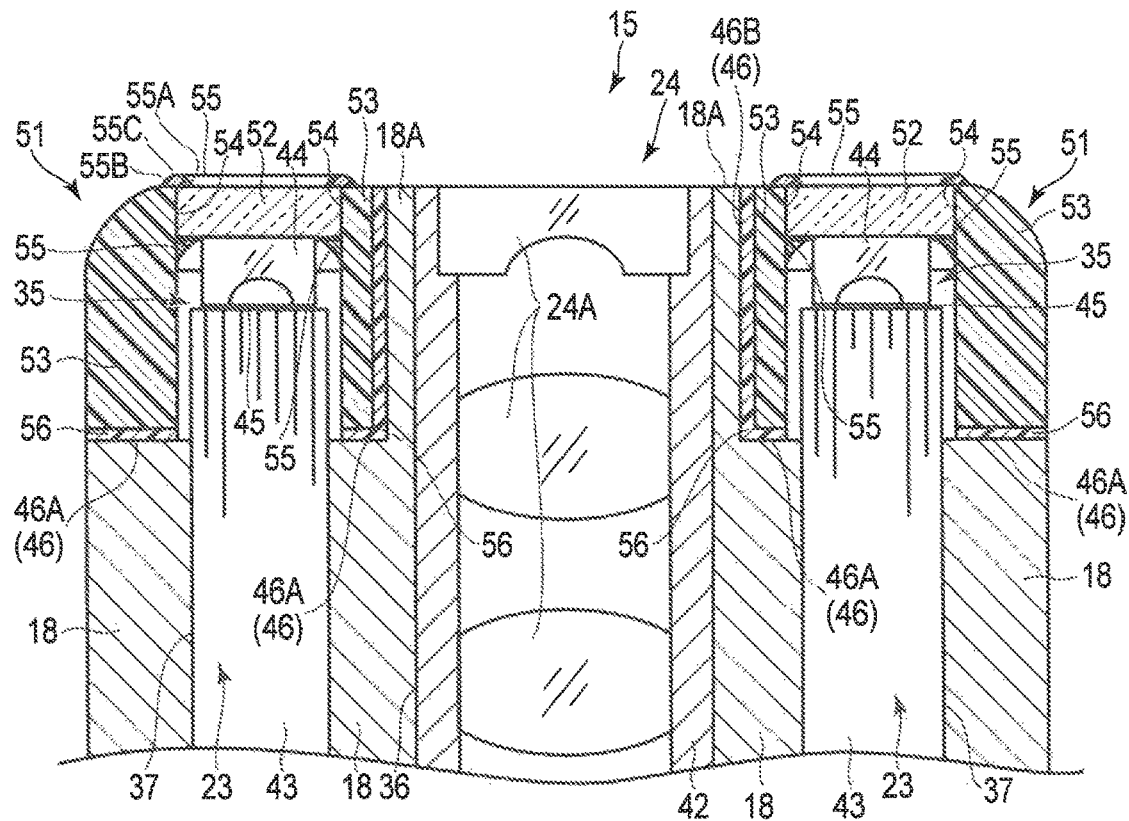
FIG. 5 is a cross-sectional view showing an endoscope system and an endoscope according to a first modification of the first embodiment.

A first modification in which part of the first embodiment is modified will be described with reference to FIG. 5. Herein, mainly the parts different from the first embodiment will be described, and the description of the parts common to the first embodiment will be omitted.

In the present modification, a resin portion 55 is applied to the distal end cover 51 on the side facing the distal end constituting portion 18, similarly to the first embodiment. In the present modification, a resin portion 55 is also provided on the opposite side from the side facing the distal end constituting portion 18, that is, on the outer periphery side of the distal end cover 51. The resin portion 55 is annularly applied to a portion including the boundary portion 54, in a manner so that the resin portion 55 corresponds to the boundary portion 54. Herein, "annular" preferably means that the ring continues, but this "annular" state is not limited to this meaning. For example, "annular" may be "substantially annular" in which the ring is interrupted at one or more positions.

The resin portion 55 is adhered to the first member 52 and the second member 53 in a manner so that the resin portion 55 extends over the first member 52 by a first fillet portion 55A and extends over the second member 53 by a second fillet portion 55B that is on the opposite side from the first fillet portion 55A. The adhesive pool 55C of the resin portion 55 located between the first fillet portion 55A and the second fillet portion 55B is arranged at a position substantially overlapping with the boundary portion 54. For the resin portion 55, for example, a thermosetting epoxy adhesive is preferably used in order to securely form the adhesive pool on the boundary portion 54, and to maintain joining strength after hardening.

According to the present modification, the distal end cover 51 can be further strengthened, since the resin portion 55 is formed on both of the inner periphery (the side facing the distal end constituting portion 18) and the outer periphery of the distal end cover 51.

Second Embodiment

Figure 6:
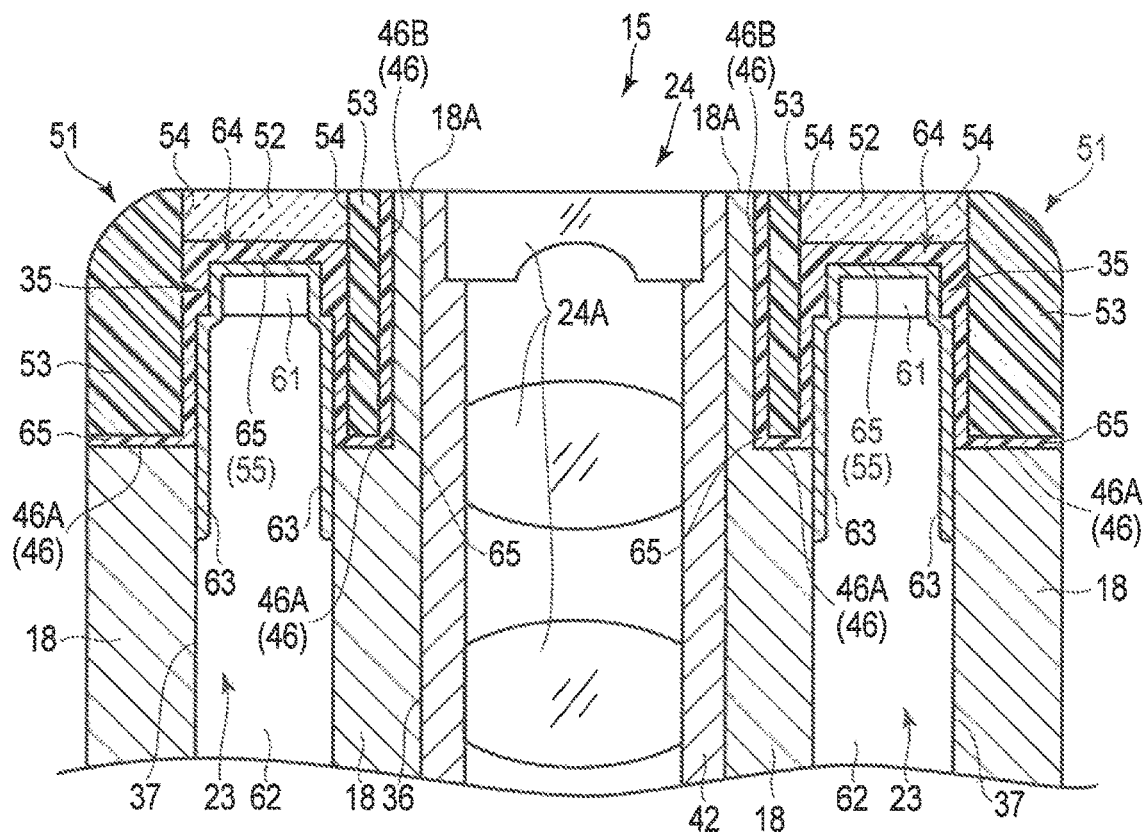
FIG. 6 is a schematic diagram showing an endoscope system and an endoscope according to a second embodiment.

A second embodiment of the endoscope system 11 will be described with reference to FIGS. 6 and 7. Here, mainly the parts different from the first embodiment will be described, and parts common to the first embodiment will not be described.

The illumination optical system 23 has a light emitting diode 61 and a holding portion 62 that supports the light emitting diode 61 and, accommodates a conducting wire for supplying power to the light emitting diode 61. The conducting wire is connected to the endoscope controller 13. A coating portion 63, in which a fluorine-based or silicone-based release agent is applied, is formed around the light emitting diode 61 and around the holding portion 62 on the distal end side. The light emitting diode 61 is an example of an illumination unit.

The second resin portion 65 fills the space (the recessed portion 35) between the distal end constituting portion 18 and the distal end cover 51. The second resin portion 65 is provided to cover the light emitting diode 61. Since the second resin portion 65 is translucent, the second resin portion 65 does not block the light from the light emitting diode 61. The second resin portion 65 is provided integrally with the resin portion 55.

Similarly to the resin portion 55, the second resin portion 65 preferably fills the space 64 between the distal end constituting portion 18 and the distal end cover 51 without leaving a gap. However, when filling the space 64 with the second resin portion 65, there may be a portion (for example, a minute recessed portion formed on the defining surface 46 of the recessed portion 35) which is not filled with the second resin portion 65, and the second resin portion 65 only has to substantially fill the space 64. For the second resin portion 65, for example, a thermosetting epoxy adhesive is preferably used in order to maintain the joining strength after hardening. The material of the second resin portion 65 is not limited thereto. The second resin portion 65 may be formed of an elastic material having rubber-like elasticity. Specifically, the second resin portion 65 may be made of, for example, an elastic material (a resin material) such as urethane foam or silicone rubber.

A method (a manufacturing method of an endoscope) of adhering the distal end cover 51 of an endoscope 12 of the second embodiment will be described with reference to FIGS. 6 and 7.

Figure 7:
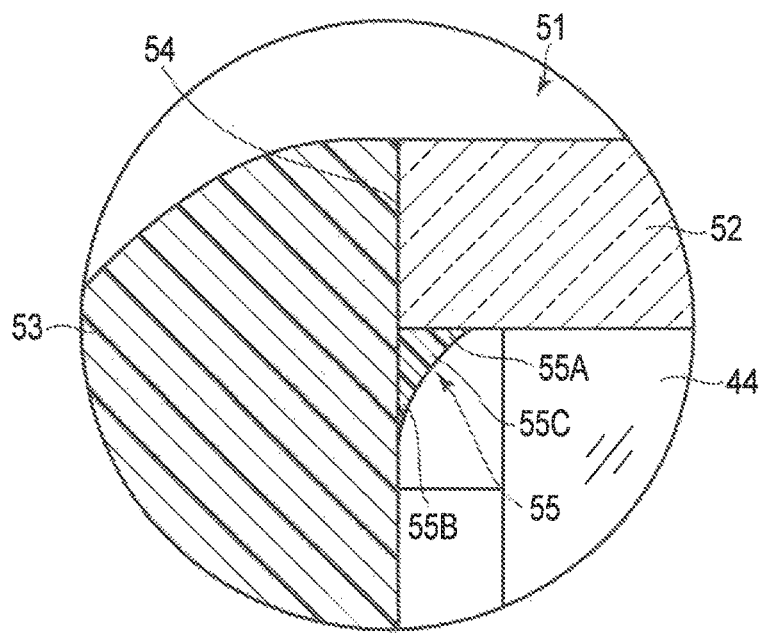
FIG. 7 is a cross-sectional view showing a step among steps of attaching a distal end cover of an endoscope according to the second embodiment shown in FIG. 6.

After completing the injection molding (two-color molding) of the distal end cover 51, an operator (or a robot) annularly applies a thermosetting epoxy adhesive to a portion including (covering) the boundary portion 54 on the side facing the distal end constituting portion 18, as shown in FIG. 7. At this time, the operator forms the resin portion 55 on the same position as in the first embodiment. Then, the thermosetting epoxy adhesive is thermally hardened to form the resin portion 55. In addition, the operator (or the robot) forms the coating portion 63, in which a release agent is applied, around the light emitting diode 61 and on the distal end side of the holding portion 62.

Thereafter, the operator applies a thermosetting epoxy adhesive to the inside of the distal end cover 51 and to the defining surface 46 of the recessed portion 35, and covers the recessed portion 35 with the distal end cover 51. In this manner, the thermosetting epoxy adhesive fills the space 64 between the distal end cover 51 and the distal end constituting portion 18. In this state, the thermosetting epoxy adhesive is thermally hardened to form the second resin portion 65 in the space 64. Thereby, the second resin portion 65 is integrated with the resin portion 55 formed in advance. Furthermore, the portion formed in the space 64 and the portion formed between the distal end cover 51 and the defining surface 46 of the recessed portion 35 are integrated in the second resin portion 65; accordingly, the sufficient adhesion strength for holding the distal end cover 51 is secured. With the above, the operation of adhering the distal end cover 51 to the distal end constituting portion 18 is completed.

It is useful to separately form the resin portion 55 and the second resin portion 65 with a time interval therebetween as in the present embodiment, in terms of preventing production of sink marks in the boundary portion 54 between the first member 52 and the second member 53 (the corner portion of the inner periphery of the distal end cover 51). In other words, when thermally hardening the resin portion 55, it is likely that the resin portion 55 hardens and shrinks to produce sink marks (cavities) at the corner portion of the inner peripheral surface of the distal end cover 51. In the present modification, the resin portion 55 is first formed to cover the boundary portion 54 inside the distal end cover 51, and the second resin portion 65 is formed in the space 64 between the defining surface 46 of the recessed portion 35 and the distal end cover 51 after the formation of the resin portion 55, thereby preventing production of sink marks in the space 64 at a position corresponding to the boundary portion 54.

The operation of the endoscope system 11 of the present embodiment will be described. In the present embodiment, since the illumination unit is constituted by the light emitting diode 61, there is a problem of how to process heat generated by the light emitting diode 61. In particular, if air remains in the space 64 between the distal end cover 51 and the defining surface 46 of the recessed portion 35 as in the first embodiment, heat may accumulate inside the light emitting diode 61 due to the high heat insulating property of air. In the present embodiment, heat generated by the light emitting diode 61 is transmitted to the side of the distal end cover 51 via the second resin portion 65. In the distal end cover 51, the heat is released to the external environment. Therefore, the heat generated by the light emitting diode 61 does not accumulate in the light emitting diode 61, which prevents damage of the light emitting diode 61 by heat.

The coating portion 63, in which a release agent is applied, is formed around the light emitting diode 61 and around the holding portion 62 on the distal end side. This makes it easier to detach the light emitting diode 61 and the holding portion 62 from the distal end cover 51 and the second resin portion 65 at the time of maintenance to exchange the light emitting diode 61 if the light emitting diode 61 breaks. As a result, the working efficiency for a repairer at the time of maintenance is improved.

According to the second embodiment, the following can be said. In the recessed portion 35, a translucent second resin portion 65 is provided to cover the illumination unit. According to this configuration, the illumination unit can be protected by the second resin portion 65, and even if an external shock is applied, damage of the illumination unit can be prevented.

The endoscope has the translucent second resin portion 65, and the second resin portion 65 fills the space 64 between the distal end constituting portion 18 and the distal end cover 51. According to this configuration, the distal end cover 51 and the distal end constituting portion 18 are integrated via the second resin portion 65. As a result, the distal end cover 51 and the distal end constituting portion 18 have a structure like one rigid body, and even if a stress exceeding expectations is applied to the boundary portion 54 between the first member 52 and the second member 53, the resin portion 55 and the second resin portion 65 are not separated from the first member 52 and the second member 53, and the boundary portion 54 can be prevented from being deformed to produce cracks in this portion.

Even if the pressure fluctuates outside the endoscope 12 when sterilizing or airlifting the endoscope 12, air does not expand or contract in the space 64 since the second resin portion 65 fills the space 64. Therefore, even if the pressure fluctuates outside the endoscope 12, a stress is not applied to the boundary portion 54 between the first member 52 and the second member 53, and production of cracks in this portion can be prevented. In particular, if a light-emitting device of the light emitting diode 61 is used as the illumination unit as in the present embodiment, it may short out due to the entrance of moisture and may break. According to the present embodiment, since the light emitting diode 61 is covered with the second resin portion 65, the light emitting diode 61 can be prevented from breaking even if cracks are produced in the boundary portion 54.

The resin portion 55 is provided integrally with the second resin portion 65 applied between the distal end constituting portion 18 and the second member 53. According to this configuration, the resin portion 55 can be supported by the second resin portion 65. This reduces the risk of the resin portion 55 falling off from the first member 52 and the second member 53, which enables the resin portion 55 to further reduce the risk of entrance of a fluid.

The endoscope has the second resin portion 65 that is applied to cover the periphery of the illumination unit, and the illumination unit includes the light emitting diode 61. According to this configuration, the second resin portion 65 can protect the light emitting diode 61 that may be damaged by, for example, moisture. As a result, even if a shock exceeding expectations is externally applied and cracks are produced in the boundary portion 54, it is possible to prevent moisture from reaching the light emitting diode 61 so as to prevent the light emitting diode 61 from breaking.

A release agent is applied around the illumination unit. According to this configuration, the illumination unit can be easily detached from the second resin portion 65 and exchanged at the time of maintenance to, for example, exchange the illumination unit constituted by the light emitting diode 61.

Furthermore, according to the present embodiment, the following can be said. The manufacturing method of the endoscope 12 is used for the endoscope 12 having the distal end constituting portion 18, the distal end cover 51 that is integrally formed to include the first member 52 and the second member 53 arranged around the first member 52, and that is attached to the distal end constituting portion 18, the resin portion 55 that prevents transmission of a fluid, and the second resin portion 65. In the method, the resin portion 55 is formed by applying a resin to a portion including the boundary portion 54 between the first member 52 and the second member 53, and by hardening the applied resin, and after that, the second resin portion 65 is formed by filling the space 64 between the distal end constituting portion 18 and the distal end cover 51 with a resin and by hardening the resin so as to be integrated with the resin portion 55. According to this configuration, it is possible to prevent production of sink marks (cavities) at a position corresponding to the boundary portion 54 in the space 64 between the distal end constituting portion 18 and the distal end cover 51. As a result, it is possible to reduce the number of endoscopes 12 which are defective due to incomplete formation of the second resin portion 65, which leads to the yield improvement of the endoscope 12.

Second Modification

A second modification in which part of the second embodiment is modified will be described with reference to FIG. 8. Herein, mainly the parts different from the second embodiment will be described, and the description of the parts common to the second embodiment will be omitted.

The second resin portion 65 fills a space 64 (a gap) between the distal end constituting portion 18 and the distal end cover 51. Similarly to the resin portion 55, the second resin portion 65 preferably fills the space 64 between the distal end constituting portion 18 and the distal end cover 51 without leaving a gap. However, when filling the space 64 with the second resin portion 65, there may be a portion (for example, a minute recessed portion formed on the defining surface 46 of the recessed portion 35) that is not filled with the second resin portion 65, and the second resin portion 65 only has to substantially fill the space. For the second resin portion 65, for example, a thermosetting epoxy adhesive is preferably used in order to maintain the joining strength after hardening. The material of the second resin portion 65 is not limited thereto. The second resin portion 65 may be formed of an elastic material having rubber-like elasticity. Specifically, the second resin portion 65 may be composed of, for example, urethane foam or silicone rubber.

A coating portion 63, in which a fluorine-based or silicone-based release agent is applied, is formed at a position on the inner surface of the distal end cover 51 (the first member 52, the second member 53) which comes into contact with the illumination unit and the distal end portion of the holding portion 62.

A method (a manufacturing method of an endoscope) of adhering the distal end cover 51 of the endoscope 12 of the second modification will be described.

Figure 8:
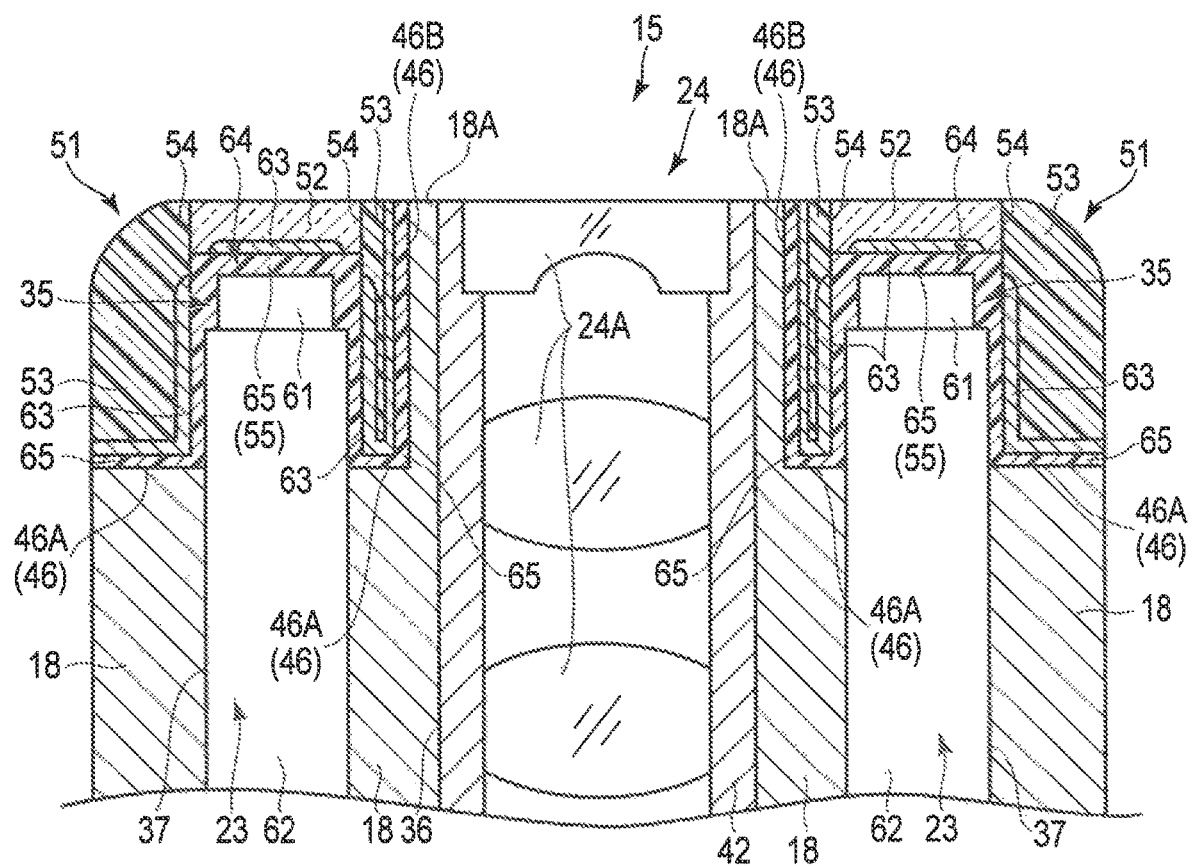
FIG. 8 is a cross-sectional view showing an endoscope system and an endoscope according to a second modification of the second embodiment.

After completing the injection molding (two-color molding) of the distal end cover 51, an operator (or a robot) annularly applies a thermosetting epoxy adhesive to the side facing the distal end constituting portion 18 of the boundary portion 54, as shown in FIG. 8. At this time, the operator applies the resin portion 55 to the same position as in the first embodiment and the second embodiment (see FIG. 7, for example). Then, the thermosetting epoxy adhesive is thermally hardened to form the resin portion 55. Thereafter, the operator applies a release agent to the inner peripheral surface of the distal end cover 51 at a position separate from the portion where the resin portion 55 (see FIG. 7) is formed, thereby forming the coating portion 63. After drying the release agent, the operator applies a thermosetting epoxy adhesive to the inner surface of the distal end cover 51 from above the release agent. At the same time, the operator applies a thermosetting epoxy adhesive to the defining surface 46 of the recessed portion 35. Then, the recessed portion 35 is covered with the distal end cover 51. In this manner, the thermosetting epoxy adhesive fills the space 64 between the distal end cover 51 and the distal end constituting portion 18. In this state, the thermosetting epoxy adhesive is thermally hardened to form the second resin portion 65 in the space 64. With the above, the operation of adhering the distal end cover 51 to the distal end constituting portion 18 is completed.

According to the present modification, a release agent is applied to the inner peripheral surface of the distal end cover 51. According to this configuration, the distal end cover 51 can be easily detached from the distal end constituting portion 18 when detaching the distal end cover 51 at the time of maintenance. At this time, a stress is not applied to the illumination unit, and the illumination unit is not damaged.

Several embodiments have been specifically described with reference to the drawings. The present invention is not limited to the above-described embodiments, and the structural elements may be modified and embodied without departing from the gist thereof. Furthermore, one endoscope system or endoscope can be realized by discretionarily combining the structural elements in the first embodiment, the first modification, the second embodiment, and the second modification described above. For example, it is naturally possible to combine the endoscope system 11 of the first embodiment with the endoscope system 11 of the first modification, and other combinations are also naturally possible.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
a distal end constituting portion provided at a distal end of an insertion section configured to be inserted into a subject;
an illumination unit that is configured to emit illumination light and is arranged in the distal end constituting portion, the illumination unit including an illumination lens or a light emitting diode;
a distal end cover that includes a first member and a second member joined to and surrounding a periphery of the first member, an entirety of the first member having a discoid shape, the distal end cover being connected to the distal end constituting portion such that the distal end cover is exposed to an external environment, and such that a space is formed between the distal end cover and the distal end constituting portion;
a first resin portion that is applied to cover a boundary portion between the first member and the second member among the space formed between the distal end cover and the distal end constituting portion; and
a second resin portion that:
is composed of an identical material to the first resin portion,
fills the space formed between the distal end cover and the distal end constituting portion so as to be provided at a position between the second member and the distal end constituting portion in a radial direction of the illumination unit, and
adheres the distal end cover, the distal end constituting portion, and the first resin portion,
wherein the identical material that is included in the first resin portion and the second resin portion is a thermosetting resin.

2. The endoscope according to claim 1, wherein the first member faces the illumination unit.

3. The endoscope according to claim 2, wherein:
the distal end constituting portion includes a recessed portion that is defined by a defining surface and is provided at a position where the illumination unit is arranged, and
the second resin portion is applied between the defining surface of the recessed portion and the distal end cover to adhere the defining surface and the distal end cover.

4. The endoscope according to claim 2, wherein the second resin portion is translucent, and fills the space so as to cover the illumination unit.

5. The endoscope according to claim 4, wherein the illumination unit includes the light emitting diode.

6. The endoscope according to claim 5, further comprising a release agent that is applied around the illumination unit.

7. The endoscope according to claim 5, further comprising a release agent that is applied to an inner peripheral surface of the distal end cover.

8. The endoscope according to claim 2, wherein the illumination unit includes:
a first portion disposed on a distal end side of the illumination unit; and
a second portion provided on a proximal end side of the first portion and having an outer diameter that is larger than an outer diameter of the first portion.

9. The endoscope according to claim 8, wherein the second resin portion fills the space so as to cover the first portion and the second portion of the illumination unit.

10. The endoscope according to claim 9, wherein the first portion of the illumination unit includes the light emitting diode (LED).

11. The endoscope according to claim 8, wherein:
the first portion of the illumination unit includes the light emitting diode, and
the second resin portion is provided in between a distal facing surface of the light emitting diode and a proximal facing surface of the first member.

12. The endoscope according to claim 1, wherein the first resin portion is further applied to an external portion of the boundary portion that is exposed to the external environment.

13. The endoscope according to claim 1, wherein:
the first member is translucent, and
the second member is arranged in immediate contact with and so as to surround the periphery of the first member, and the second member is configured to prevent transmission of light.

14. The endoscope according to claim 1, wherein the first member and the second member are a two-color molded resin.

15. A method of manufacturing the endoscope according to claim 1, the method comprising: forming the first resin portion by applying a first resin so as to cover the boundary portion between the first member and the second member among the space formed between the distal end cover and the distal end constituting portion, and by hardening the applied first resin; and then forming the second resin portion by filling the space between the distal end constituting portion and the distal end cover with a second resin, and by hardening the filled second resin so as to be integrated with the first resin portion.

16. The endoscope according to claim 1, wherein the first resin portion covers a surface of the first member that is transverse to a surface of the second member covered by the first resin portion.

17. An endoscope comprising:
a distal end constituting portion provided at a distal end of an insertion section configured to be inserted into a subject;
an illumination unit that is configured to emit illumination light and is arranged in the distal end constituting portion, the illumination unit including an illumination lens or a light emitting diode;
a distal end cover that includes a first member and a second member joined to and surrounding a periphery of the first member, an entirety of the first member having a discoid shape, the distal end cover being connected to the distal end constituting portion such that the distal end cover is exposed to an external environment, and such that a space is formed between the distal end cover and the distal end constituting portion;
a first resin portion that is applied to cover a boundary portion between the first member and the second member among the space formed between the distal end cover and the distal end constituting portion; and a second resin portion that:
- is composed of an identical material to the first resin portion,
- fills the space formed between the distal end cover and the distal end constituting portion so as to be provided at a position between the second member and the distal end constituting portion in a radial direction of the illumination unit, and
- adheres the distal end cover, the distal end constituting portion, and the first resin portion, wherein the first resin portion is provided integrally with the second resin portion.

18. An endoscope comprising:

a distal end constituting portion provided at a distal end of an insertion section configured to be inserted into a subject;

an illumination unit that is configured to emit illumination light and is arranged in the distal end constituting portion, the illumination unit including an illumination lens or a light emitting diode;

a distal end cover that includes a first member and a second member joined to and surrounding a periphery of the first member, an entirety of the first member having a discoid shape, the distal end cover being connected to the distal end constituting portion such that the distal end cover is exposed to an external environment, and such that a space is formed between the distal end cover and the distal end constituting portion;

a first resin portion that is applied to cover a boundary portion between the first member and the second member among the space formed between the distal end cover and the distal end constituting portion; and a second resin portion that:
- is composed of an identical material to the first resin portion,
- fills the space formed between the distal end cover and the distal end constituting portion so as to be provided between a proximal facing surface of the second member and a distal facing surface of the distal end constituting portion in an axial direction of the distal end constituting portion, and
- adheres the distal end cover, the distal end constituting portion, and the first resin portion.

\* \* \* \* \*